United States Patent [19]

Bourgeois et al.

[11] Patent Number: 5,716,392
[45] Date of Patent: Feb. 10, 1998

[54] MINIMALLY INVASIVE MEDICAL ELECTRICAL LEAD

[75] Inventors: Ivan Bourgeois, Heusy-Verviers, Belgium; Noud Bakels, Simpelveld; Paulus Van Venrooij, Hoensbroek, both of Netherlands

[73] Assignee: Medtronic, Inc., Minneapolis, Minn.

[21] Appl. No.: 583,358

[22] Filed: Jan. 5, 1996

[51] Int. Cl.⁶ ............................................. A61N 1/05
[52] U.S. Cl. ................. 607/132; 128/642; 606/222; 606/224
[58] Field of Search ......................... 607/116, 132, 607/120, 126, 129, 133; 128/642; 606/222, 224

[56] References Cited

U.S. PATENT DOCUMENTS

| | | | |
|---|---|---|---|
| 2,865,376 | 3/1958 | Pellier et al. | 606/222 |
| 4,444,207 | 4/1984 | Robicsek | 607/132 |
| 4,524,771 | 6/1985 | McGregor et al. | 606/223 |
| 4,901,722 | 2/1990 | Noguchi | 606/223 |
| 5,059,207 | 10/1991 | Shah | 606/223 |
| 5,100,431 | 3/1992 | Buster et al. | 606/222 |
| 5,423,872 | 6/1995 | Cigaina | 607/40 |
| 5,423,876 | 6/1995 | Camps et al. | 607/132 |
| 5,433,728 | 7/1995 | Kim | 606/224 |
| 5,450,739 | 9/1995 | Bogart et al. | 72/133 |
| 5,489,294 | 2/1996 | McVenes et al. | 607/132 |

*Primary Examiner*—Scott M. Getzow
*Assistant Examiner*—Kennedy J. Schaetzle
*Attorney, Agent, or Firm*—Michael J. Jaro; Harold Patton

[57] ABSTRACT

A medical electrical lead which may be introduced using a thorascope and is used to electrically stimulate tissue, such as a heart. The lead of the present invention has a "ski-shaped" needle, a strand of between 1–5 cm. attached to the needle, an electrode attached to the strand, and an insulated lead body attached to the electrode. In addition, a test wire is also attached to the needle to permit the electrical characteristics of tissue to be ascertained before the lead is fully inserted. In an alternate embodiment the strand may feature a fixation helix. Due to the shape of the needle and the relatively short strand, the lead is particularly suitable for implantation to a heart using minimally invasive techniques, such as through a trocar.

15 Claims, 13 Drawing Sheets

FIG. 23

MINIMALLY INVASIVE MEDICAL ELECTRICAL LEAD

FIELD OF THE INVENTION

The present invention generally relates to medical electrical leads, and more particularly, to a medical electrical lead which may be implanted into a body organ or tissue using minimally invasive techniques, such as thorascopically, laproscopically or endoscopically.

BACKGROUND OF THE INVENTION

Electrical stimulation of body tissue and organs is often used as a method of treating various pathological conditions. Such stimulation generally entails making an electrical contact between body tissue and an electrical pulse generator through use of one or more stimulation leads. Various lead structures and various techniques for implanting these lead structures into body tissue and particularly the heart have been developed.

For example, a transvenous endocardial lead establishes electrical contact between an electrical pulse generator and heart through placement of a lead in the venous system. Specifically, a transvenous endocardial lead is passed through a vein, with the assistance of a fluoroscope, into the heart where it may be held in contact with the endocardium by the trabeculae of the heart chamber, such as the ventricle.

There are, however, disadvantages to transvenous leads including: possible damage to the vein, such as perforation or laceration during insertion; possible failure to securely attach and maintain electrical contact with the heart; possible perforation of the heart wall by the lead; and because direct visual inspection of the lead placement is not possible, possible improper lead placement in the heart. In addition, the usage of a fluoroscope to visualize lead position carries its own set of risks to both the patient as well as to the physician.

Besides these disadvantages there are additional situations in which the installation of a transvenous endocardial pacing lead is either not feasible or not recommended. These situations include the case when the area to be stimulated is the left side of the heart.

The left side of the heart is presently not available for the implantation of chronic or long term transvenous leads due to risk of thrombus or clot formation. In particular, blood flows through the right side of the heart (atrium and ventricle), through the lungs, through the left side of the heart (atrium and ventricle) and then through the rest of the body, including the brain, before returning again to the right side of the heart. Implanted objects, however, often cause minor blood clots and thrombus to form in the blood. These may, on occasion, dislodge and be released into the bloodstream. Because the blood circulates directly from the left atrium and ventricle to the brain, any clots, however minor, could have serious consequences if they were to reach the brain, e.g. a stroke. In contrast, any clots released from an object implanted in the right side of the heart would simply travel to the lungs, where they would lodge without any serious risk. Thus at present, chronic transvenous leads may not be safely implanted within the left side of the heart.

In spite of the difficulties, there remains a great need to be able to electrically stimulate or sense or both the left side of the heart. The most obvious reason is the left side of the heart accounts for the majority of hemodynamic output. For example, the left ventricle has a greater wall thickness (10–20 mm as compared to 1–5 mm) than the right side. This, of course, is reasonable given that the left side of the heart must pump blood throughout the body while the right side only pumps blood through the lungs.

Because the left side is relatively more important for hemodynamic output, not surprisingly various pathologies may be better treated through stimulation on the left side of the head. For example, in patients with dilated cardiomyopathy, electrical stimulation of both the right side and the left side of the head has been shown to be of major importance to improve the patient's well-being and manage head failure. See, for example, Cazeau et al., "Four Chamber Pacing in Dilated Cardiomyopathy," PACE, November 1994, pgs. 1974–79. See also Brecker and Fontainem, St. et al., "Effects Of Dual Chamber Pacing With Shod Atrioventricular Delay In Dilated Cardiomyopathy," Lancet November 1992 Vol 340 p1308–1312; Xiao H. B. et al., "Effect Of Left Bundle Branch Block On Diastolic Function In Dilated Cardiomyopathy," Br. Head J 1991.66(6) p 443–447; and Fontaine G. et al, "Electrophysiology Of Pseudofunction," CI.Meere (ed) Cardiac pacing, state of the art 1979, Pacesymp, 1979 Montreal.

At present there are several techniques for implanting a lead onto or into the left side of the head. First, of course, is through general thoracic surgery; either via a median sternotomy; intercostal approach; or, in a more limited procedure, a sub-xiphoid approach. All of these procedures, however, involve major surgery which may be painful and dangerous for the patient, as well as extremely costly. The sub-xiphoid approach, moreover, only permits limited access to the anterolateral surface of the left ventricle and does not provide any access to the left atrium. In short, what is needed is a simpler, safer and more effective way of accessing the left side of the head, including both the atrium and the ventricle, with a medical electrical lead.

SUMMARY OF THE INVENTION

It is thus an object of the present invention to provide a minimally invasive system and method for implanting a medical electrical lead.

It is a further object of the present invention to provide a medical electrical lead which will simply and safely stimulate both the right and the left side of the head, including the atrium and the ventricle.

Briefly, the above and further objects and features of the present invention are realized by providing a new and improved minimally invasive medical electrical lead. The lead may be introduced using a trocar and is used to electrically stimulate tissue, such as a heart. The lead of the present invention has a "ski-shaped" needle, a strand of between 1–5 cm. attached to the needle, an electrode attached to the strand, and an insulated lead body attached to the electrode. In addition, a test wire is also attached to the needle to permit the electrical characteristics of tissue to be ascertained before the lead is fully inserted. In an alternate embodiment the strand may feature a fixation helix. Due to the shape of the needle and the relatively short strand, the lead is particularly suitable for implantation to a heart using minimally invasive procedures, such as trocar and a thorascope.

BRIEF DESCRIPTION OF THE DRAWINGS

The above and other options, features and advantages of the present invention will be more apparent from the following more particular description thereof, presented in conjunction with accompanying drawings, wherein.

DETAILED DESCRIPTION OF THE PREFERRED EMBODIMENT

For the purposes of this specification and claims, the term "lead" is used herein in its broadest sense and includes a stimulation lead, a sensing lead, a combination thereof or any other elongated member, such as a catheter, which may usefully be introduced into a body.

THE PRIOR ART LEAD

Figure 1:
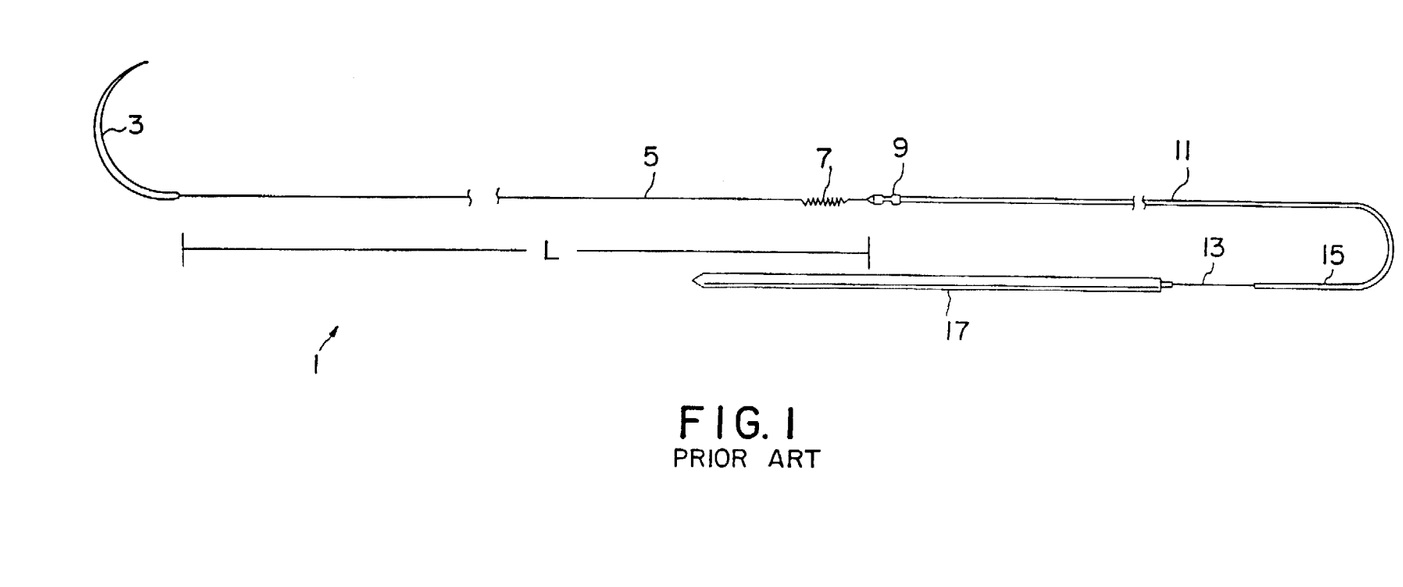
FIG. 1 is a plan view of a prior art medical electrical lead.

FIG. 1 is a plan view of a prior art medical electrical lead. As seen, lead 1 has a curved needle 3 attached to strand 5. Strand 5 features helix or pig-tail 7 to assist in fixing lead into the head tissue. Attached to proximal end of strand 5 is electrode 9. Electrode 9, in turn is attached to lead body 11. Lead body 11 consists of a conductor 13 and insulative sleeve 15 (shown here in partial cut-away.) Pin 17 is provided on proximal end.

Figure 2:
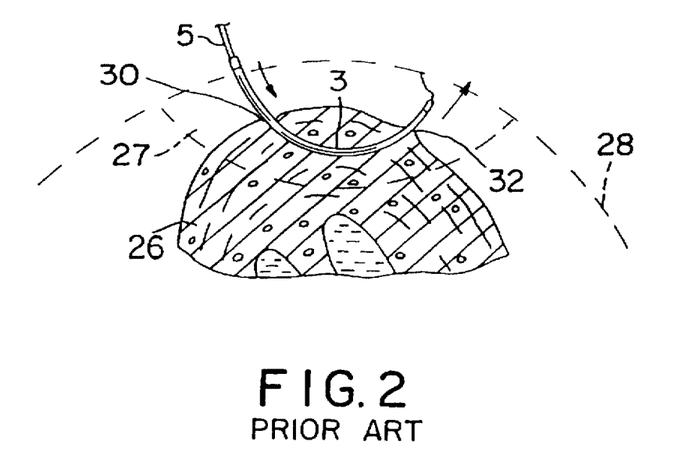
FIGS. 2-4 show an implantation of a prior art medical electrical lead.
Figure 3:
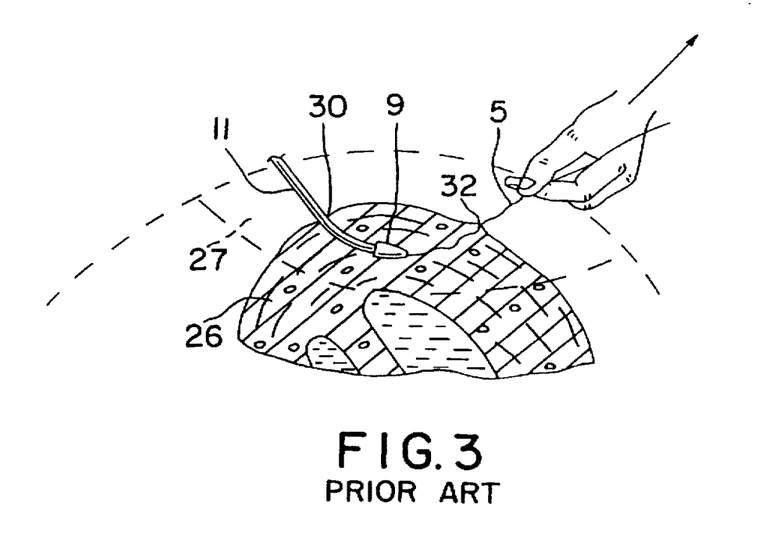
Figure 4:
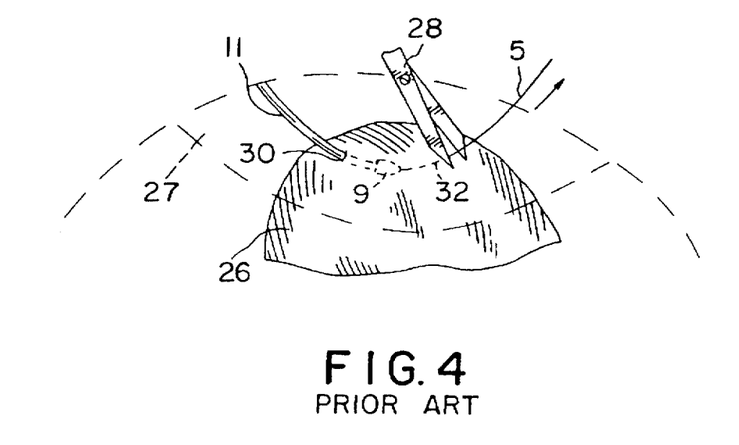

FIGS. 2-4 show an implantation of a prior art medical electrical lead. As seen in FIG. 2, insertion requires first achieving direct access to head 26. Access generally entails achieving a fairly large opening 27 (shown in phantom) into chest wall 28 or sub-xiphoid of the patient, as described above. Once sufficient access is achieved, then the myocardium of heart 26 is entered at first location 30 and exited at second location 32 by curved needle 3 being moved in the direction shown. Needle 3 is curved because to provide ease of insertion as well as to avoid perforating the cardiac wall. As can be appreciated, because direct access to heart 26 is required for prior art lead 1 and needle 3 in particular, opening 27 must be relatively large, generally on the order of between 1 and 20 cm., depending on the physician and patient as well as the approach used, i.e. thoracotomy or sub xiphoid.

FIG. 3 shows the manner in which electrode 9 is properly positioned. Strand 5 is manually pulled from second location 32 until electrode 9 to which it is attached is pulled into the orifice through location 30. Notice that electrode 9 and pig tail 7 are located completely within myocardial tissue. Past types of leads, such as the Medtronic Model 6500 temporary heart wire, had a length of strand 18 cm. in length. A strand of this length was provided to permit the surgeon to manipulate the needle and properly position the lead by hand.

FIG. 4 shows removal of the excess surgical thread. Specifically, while tension is continuously supplied, surgical thread 18 is severed by cutting instrument 28 near second location 32. Thus as seen, the prior art lead required a relatively large opening through the chest wall to permit the direct handling of the lead by hand. Such a relatively large opening, of course, creates a larger area in which the patient must heal. Thus the present invention is designed so as to permit a lead to be introduced into the heart using a minimally invasive technique.

MEDICAL ELECTRICAL LEAD ACCORDING TO THE PRESENT INVENTION

The medical electrical lead according to the present invention may be introduced into the body without requiring a elongate incision through the chest wall or by requiring access through a vein. The lead may be configured to be either a temporary lead or a permanent lead. In particular, the medical electrical lead according to the present invention features a needle and strand which may be introduced into the heart through a trocar. The needle features a curved section and a straight section while the strand is extremely short as compared to prior art leads. Through the unique properties offered by the needle and strand together, the medical electrical lead of the present invention may be introduced into the body using a minimally invasive technique.

Figure 5:
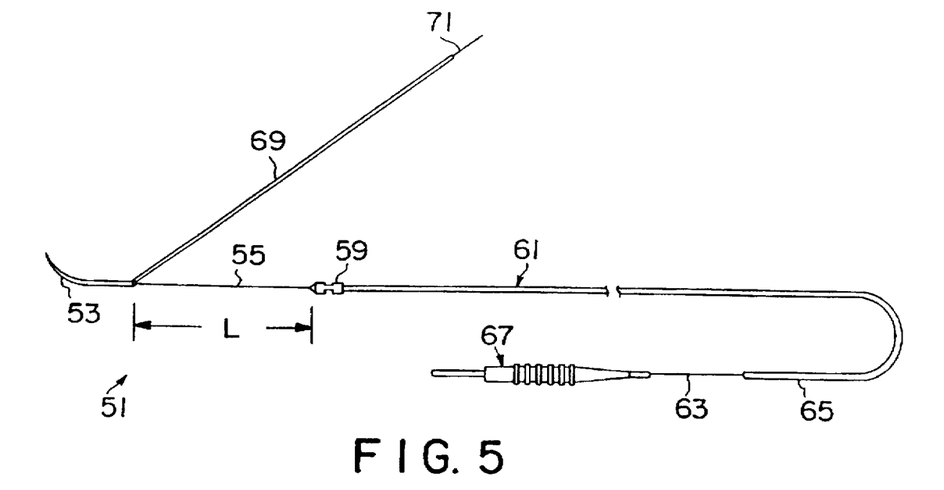
FIG. 5 shows a medical electrical lead according to the present invention.

FIG. 5 shows a permanent lead 51 according to the present invention. As seen lead 51 has a needle 53 attached to strand 55. Strand 55, in turn, is attached to electrode 59. In the preferred embodiment electrode 59 is polished platinum. Of course other types of electrode finishes may be provided, such as an electrode finished with platinum black, as is well known in the art. Of course other types of finishes may be provided, such as iridium oxide. Electrode 59, in turn is attached to lead body 61.

Lead body 61 consists of a conductor 63 (shown here in cut away section) and insulative sleeve 65. In the preferred embodiment conductor 63 is tinsel wire of MP35N and insulative sleeve is made of silicone. Of course, other constructions for lead body 61 may be used, such as other types of conductors, such as a coil, and other types of insulative sleeves, such as polyurethane. Pin 67 is provided on proximal end. In the preferred embodiment pin 67 meets the standard IS-1 criteria used by the pacing industry. Also attached to needle 53 is test wire 69. Test wire 69 is constructed from a conductor (not shown) and insulative sheath in any acceptable manner. Attached at end of test wire 69 is test pin 71, to permit test wire 69 and thus needle 53 to be temporarily connected to a pulse generator. Needle 53 may then be touched against the heart tissue at various locations so as to ascertain the electrical characteristics of a local area of heart tissue, as is well known in the art. Once a suitable area of tissue is detected the test wire is removed and the needle introduced into the heart tissue to implant lead. Further details of the construction and use of a test wire may be found in the U.S. Pat. No. 5,425,751 of Baetan et al. "Method and Apparatus for Optimum Positioning of a Muscle Stimulating Implant" incorporated heroin by reference. Through this configuration the proper location for the lead may be detected without first having to actually insert the lead into the tissue, thereby minimizing damage to the tissue as well as minimizing the formation of arrhythmia's.

METHOD OF IMPLANTING THE LEAD

As discussed above lead 1 is implanted using a minamally invasive technique. In particular the unique shape of needle 53 and relatively short strand 55 permit the lead of the present invention to be implanted through a trocar. The thorascope and trocar may be of any suitable design, such as from Ethicon Endo-Surgery, a division of Johnson & Johnson, such as the II Trocar Model TS 111, Stapler ECS 21 or Ligaclip™ ERCA ER 220. The Endoscopic equipment is made by Fujinon Inc. Series 200, Olympus America Inc. 130 series Karl Storz Endoscopy-America, Inc.

Figure 6:
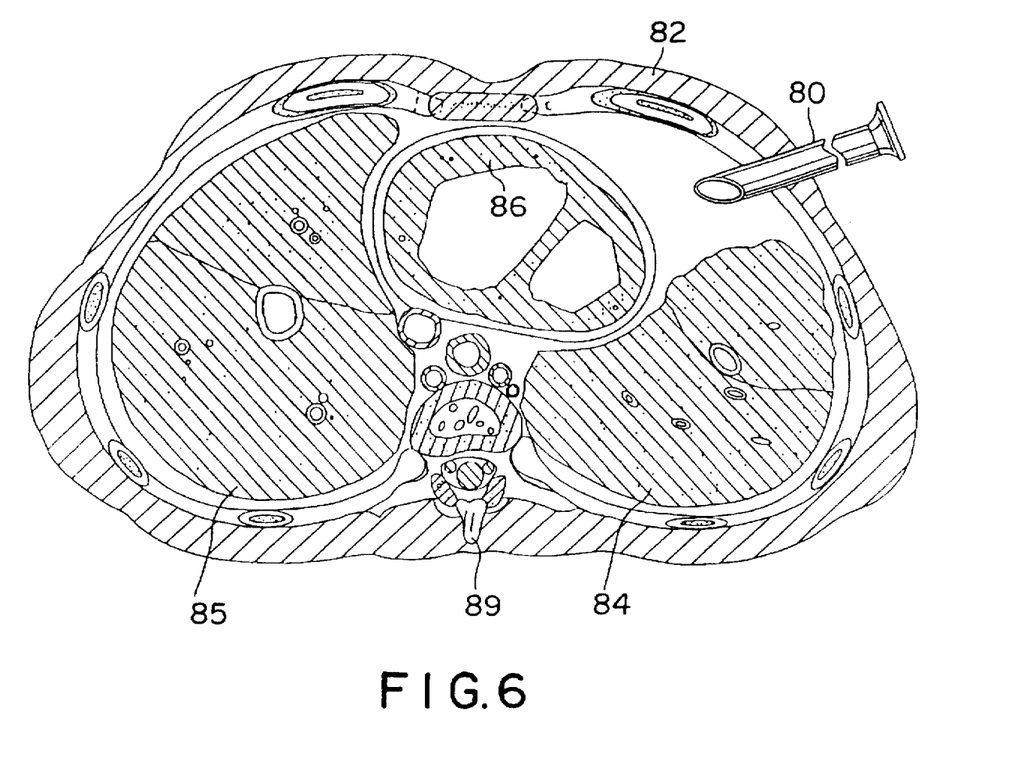
FIG. 6 is a sectional view of a human body showing a trocar disposed through the chest wall through which a lead may be implanted into the heart.

As best seen in FIG. 6, lung 84 is at least partially deflated or collapsed to provide better access to the surface of heart 86. Lung 84 may be collapsed using any of the many acceptable techniques. Next, trocar 80 is introduced through chest wall 82. As seen the chest or thoracic cavity contains lungs 84 and 85 and heart 86. Also seen is spine 89.

Figure 7:
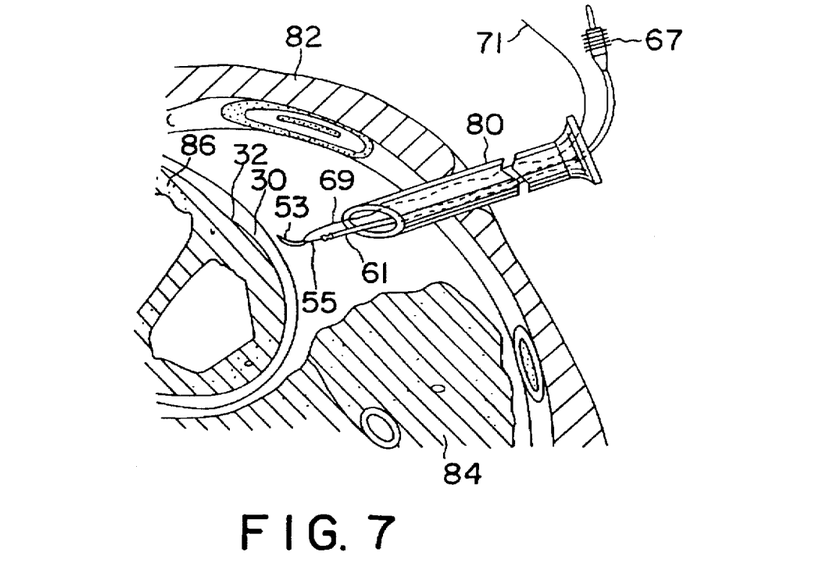
FIG. 7 is a sectional view showing a trocar disposed through the chest wall of a patient, the trocar having a lead according to the present invention disposed therethrough.

Once access to heart 86 is achieved, lead 51 is introduced through trocar 80, as best seen in FIG. 7. Next needle 53 is positioned against heart 86. At this point, due to test wire 69 being electrically coupled to needle 53, heart 86 may be mapped such that the electrical properties of the tissue are evaluated. Once a suitable site is selected, test wire 69 is removed by cutting it at a location near needle 53. Needle 53 is then introduced through heart tissue at first location 30 and exited at second location 32. Strand 55 is then pulled from second location 32 until electrode 59 to which it is attached is pulled into the orifice at location 30.

Figure 8:
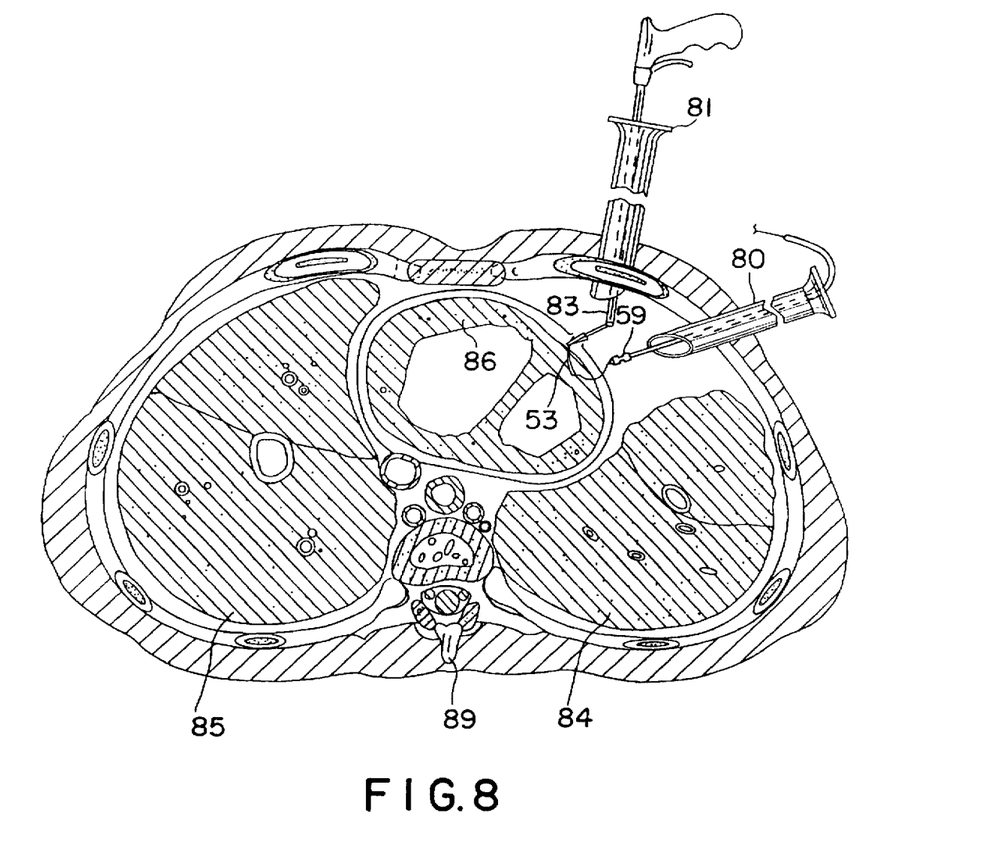
FIG. 8 is a sectional view showing a second trocar having a forceps used to handle the lead of the present invention.

As seen in FIG. 8 strand 55 is pulled through the use of a second trocar 81 having forceps 83 as is well known in the art.

Figure 9:
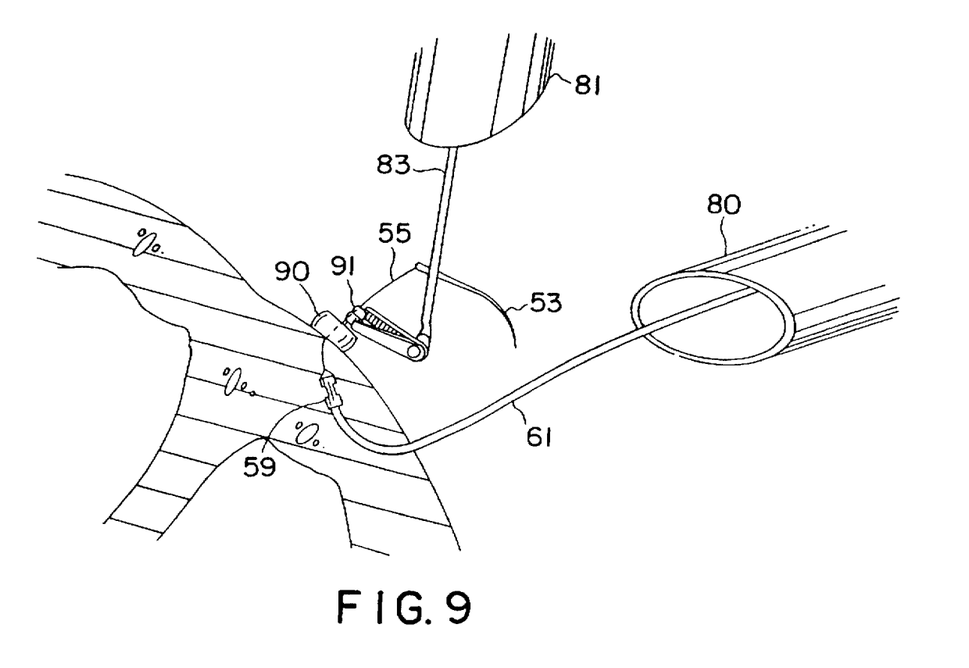
FIG. 9 is a detailed plan view of a fixation disk being attached through a crimp clip to the strand of the lead according to the present invention.

Once electrode 59 is properly positioned, fixation disk 90 is placed along strand 55 and crimp clip 91 place about strand 55 and distal to electrode 59, as seen in FIG. 9. Fixation disk 90, crimp clip 91 and strand 55 cooperate to maintain electrode 59 in place.

Figure 10:
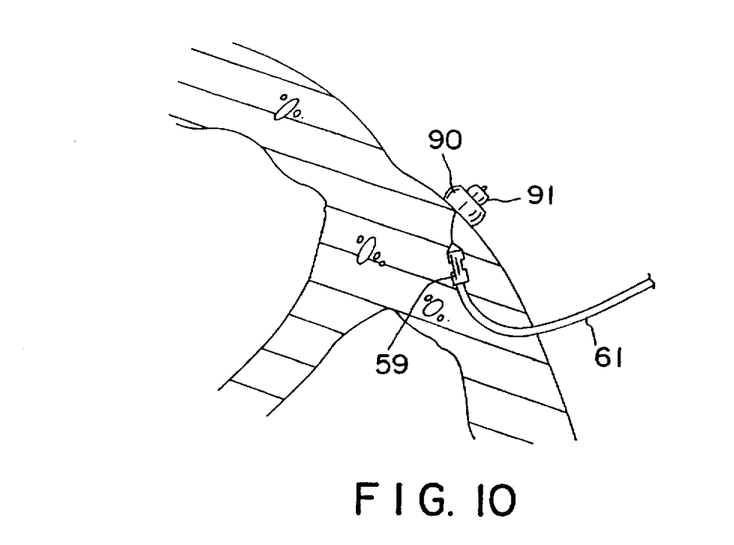
FIG. 10 is a detailed plan view of the fixation disk attached through crimp clip to the strand of the lead according to the present invention.

Once crimp clip 91 is positioned excess strand 55 is cut proximate crimp clip 91 and removed through trocar, as best seen in FIG. 10.

Figure 11:
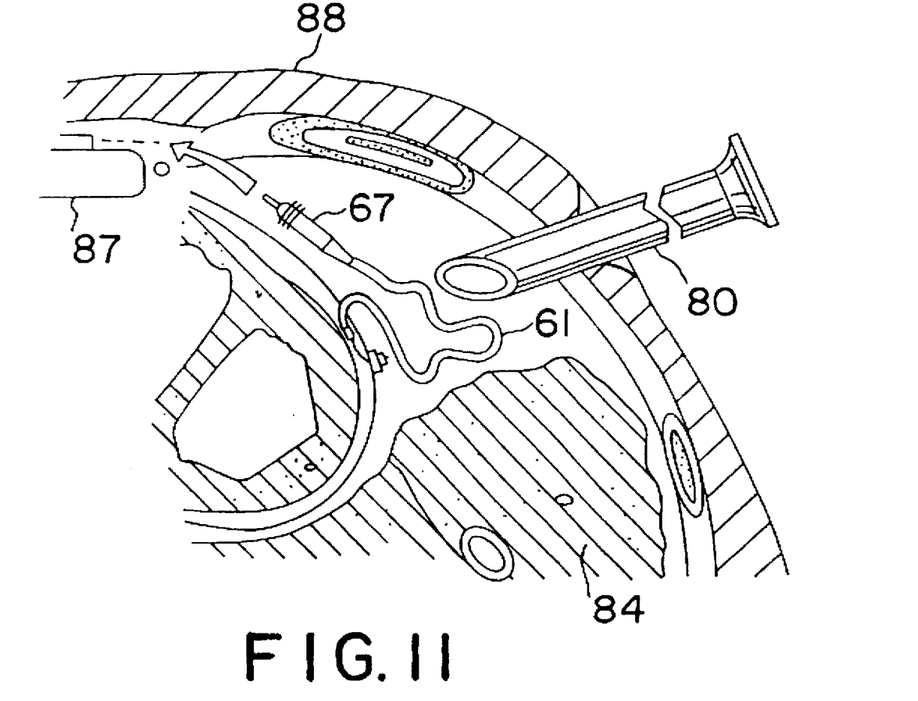
FIGS. 11 and 12 show the connector pin tunneled to the pulse generator pocket and connected to pulse generator within a patient.
Figure 12:
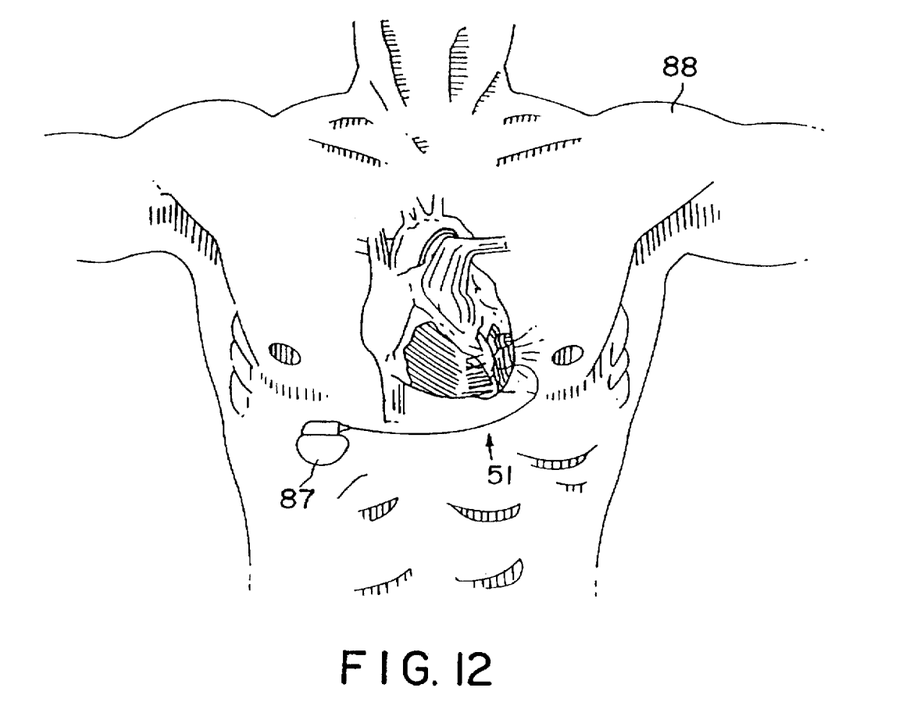

Finally, as depicted in FIGS. 11 and 12, pin 67 is tunneled to the pulse generator pocket and connected to pulse generator 87 within patient 88, followed by removal of the trocars, and reinflation of lung 84.

Figure 13:
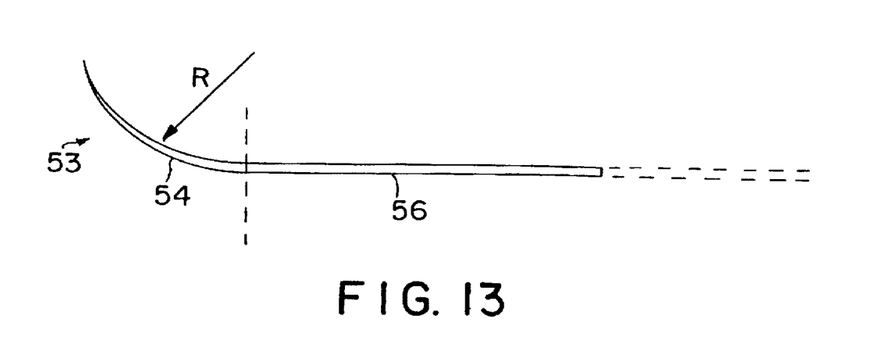
FIG. 13 is a plan view of the needle used in the lead of the present invention.

As seen, lead 51 of the present invention may be inserted using a thorascope due to the unique combination of needle 53 and strand 55. In particular the relatively small bend of needle 53 permits lead 51 to be introduced through a small diameter trocar. As seen in FIG. 13 needle 53 essentially has two portions; a first curved portion 54 and a second straight portion 56. In the preferred embodiment first curved portion 54 has a radius of curvature "R" of 13 mm over 30 degrees and second straight portion 56 has a length of between 13 and 25 mm. Alternatively, a curved needle with a radius of curvature of 11 mm over 170 degrees or less may also be used.

As best seen in FIG. 5 strand 55 is between 1 to 10 cm. in length L with 5 cm. preferred. This is in contrast to the standard strand length of 18 cm. as seen in the prior art lead shown in FIG. 1. This length of strand 55 and type of needle 53 permit the lead of the preferred embodiment to be introduced using only a 10 mm trocar. Thus only an incision of 10 mm long need be made to insert the lead. Of course, 2 to 3 other incisions must also be made for the forceps and other know thorascopic equipment. None of these incisions, however, are greater than 10 mm in length. It is even conceivable only one additional incision is necessary if the electrode is inserted using the same trocar as that used for the forceps.

Figure 14:
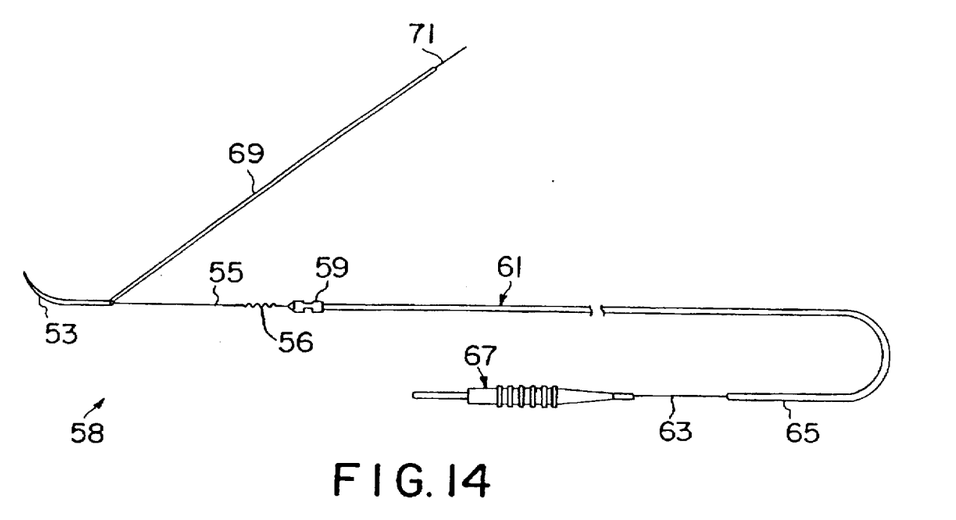
FIG. 14 shows an alternate embodiment of a lead according to the present invention.

An alternative embodiment of a lead 58 according to the present invention is seen in FIG. 14. As seen lead 58 is identical to that shown in FIG. 5 but for the inclusion of helix 56 in strand 55. Helix 56 functions to assist in fixing electrode 59 within tissue, as is well know in the art, without (or with) the use of crimp clip 90.

Figure 15:
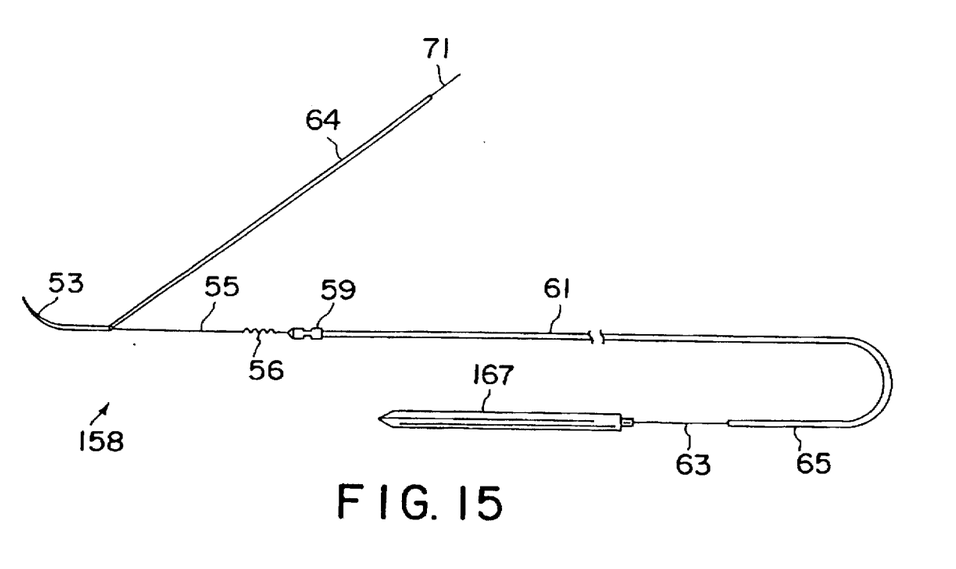
FIG. 15 shows a further alternate embodiment of a lead according to the present invention.

An further alternative embodiment of a lead 158 according to the present invention is seen in FIG. 15. Lead 158 is intended for temporary implantation. In particular lead 158 is identical to that shown in FIG. 5 but for the inclusion of splittable needle 167 in place of connector pin 67. Splittable needle 167 permits proximal end of lead 167 to be exited through the chest wall and skin to a temporary pulse generator, as well known in the art.

Implantation of 158 is as follows. As discussed above in regards to FIG. 6, lung 84 is at least partially deflated or collapsed to provide better access to the surface of heart 86. Lung 84 may be collapsed using any of the many acceptable techniques. Next, at least one trocar is introduced through chest wall 82.

Figure 16:
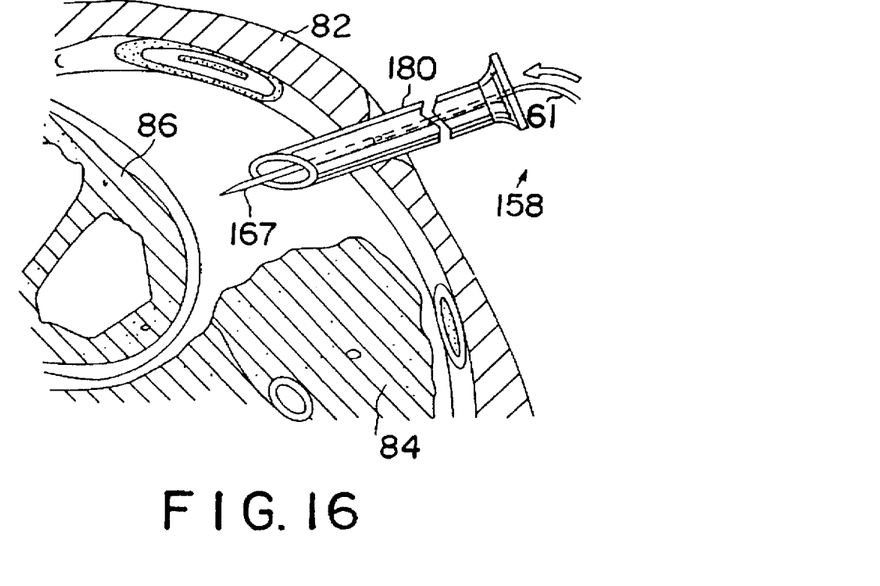
FIGS. 16-21 show the implantation of the an alternate embodiment lead shown in FIG. 14.

Turning now to FIG. 16, once access to heart 86 is achieved, lead 158 is introduced through trocar 180. In particular proximal end of lead 158 having splittable needle 167 is introduced through trocar 180.

Figure 17:
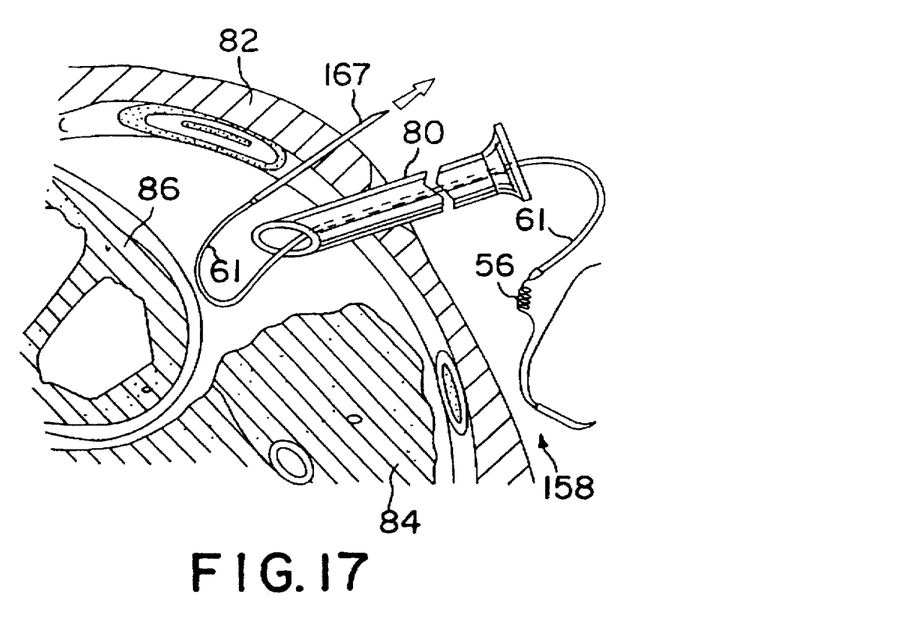

As seen in FIG. 17, once inside the thoracic cavity, the splittable needle 167 is moved from the inside of the thoracic cavity to the outside through the chest wall. This is done to permit the lead to be coupled to an external stimulator using splittable needle 167 as is well known in the art.

Figure 18:
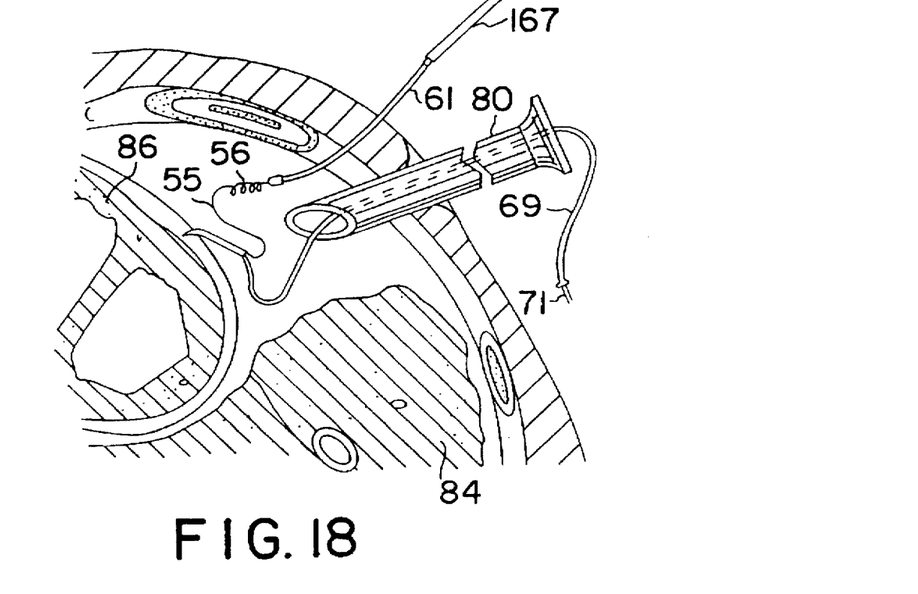

Next, turning to FIG. 18, the needle 167, strand 55 and lead body 61 of lead are brought in the thoracic cavity through the trocar 80 while the test wire 69 remains disposed through trocar, and in particular test pin 71 remains outside of the body. At this point, due to test wire 69 being electrically coupled to needle 53, heart 86 may be mapped such that the electrical properties of the tissue are evaluated.

Figure 19:
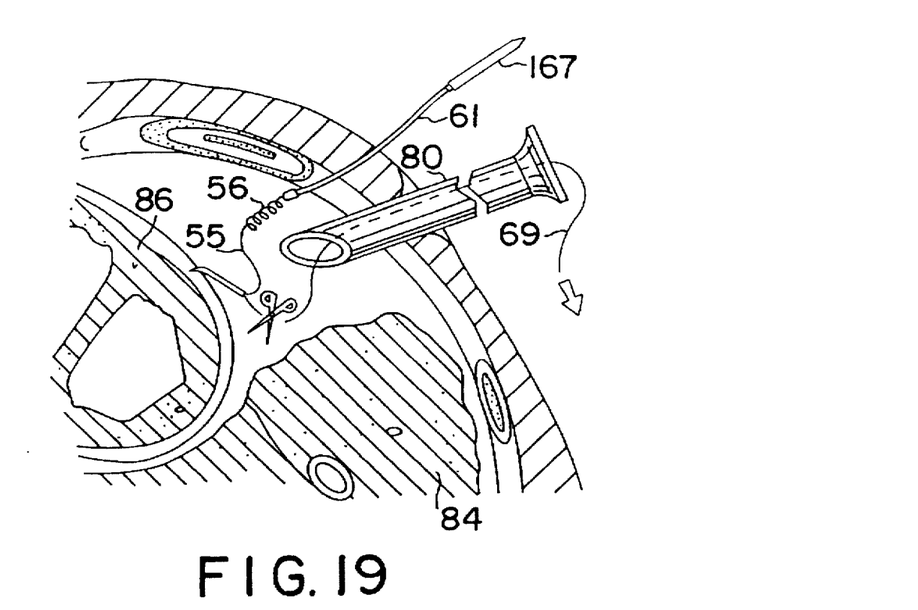

Once a suitable site is selected, test wire 69 is removed by cutting it at a location near needle 53, as seen in FIG. 19.

Figure 20:
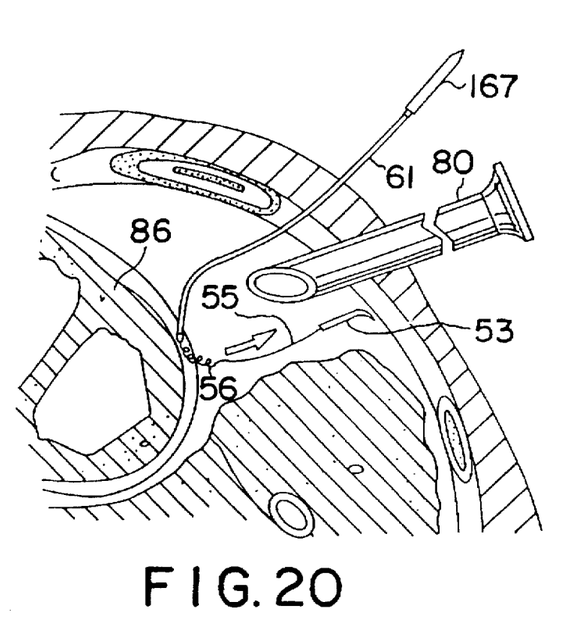

As best seen in FIG. 20, once a suitable site has been selected and test wire 69 removed, needle 53 is then introduced through heart tissue at first location 30 and exited at second location 32. Strand 55 is then pulled from second location 32 until electrode 59 to which it is properly positioned.

Figure 21:
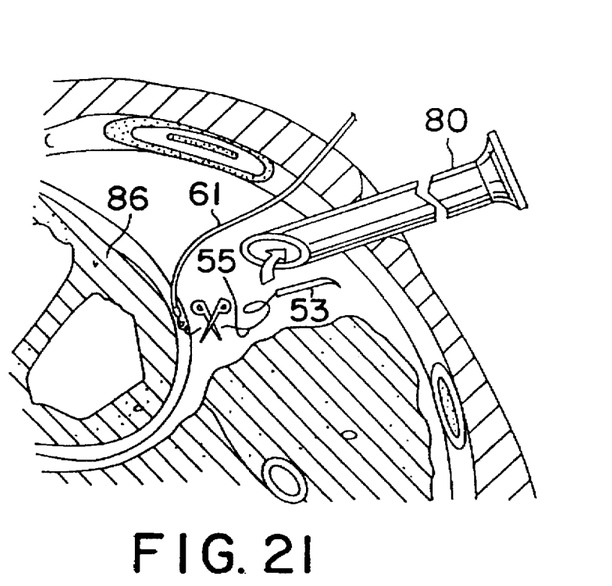

Once electrode 59 is positioned, excess strand 55 is cut and removed through trocar, as depicted in FIG. 21.

Figure 22:
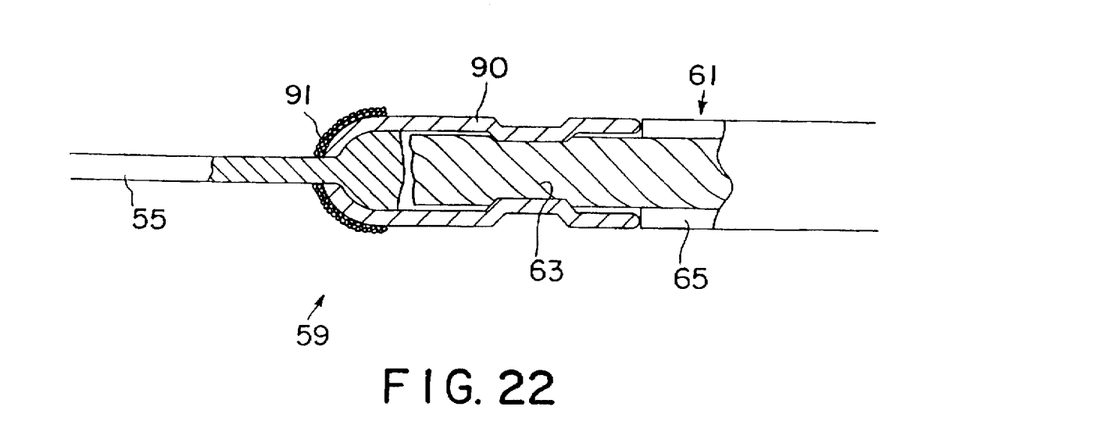
FIG. 22 is a detailed cross-sectional view of electrode used in the lead of the present invention.

FIG. 22 is a detailed cross-sectional view of electrode used in the lead of the present invention. As seen, electrode 59 may be constructed through a metallic crimping sleeve 90 against conductor 63. At the distal end of crimping sleeve 90 there may be a sintered porous electrode surface 91. Sintered porous electrode surface 91 may be fashioned from any acceptable materials, such as a spherical platinum powder having a platinum black finish as is better described in U.S. Pat. No. 5,408,744 of Gates, incorporated herein by reference.

Figure 23:
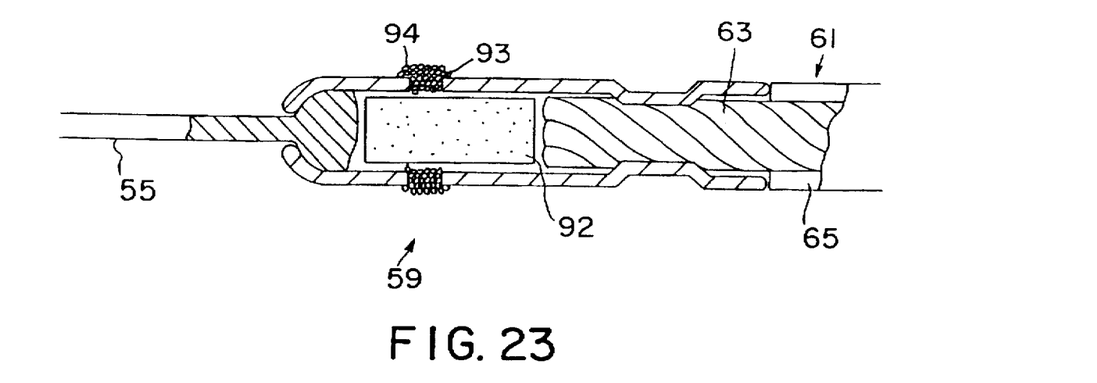
FIG. 23 is an alternate embodiment of an electrode used in the lead according to the present invention The drawings are not necessarily to scale.

FIG. 23 is an alternate embodiment of an electrode used in the lead according to the present invention. As seen, electrode 59 may be fashioned from metallic crimp sleeve having an internal volume into which a drug eluding substrate may be positioned. As seen, a monolithic controlled release device (MCRD) 92 is positioned within the volume of crimp sleeve 90. Crimp sleeve 90 further features a series of holes 93. Each hole 93 is covered by a sintered porous material 94, such as a spherical platinum powder having a platinum black finish, as described in the above-mentioned patent of Gates. Although, in the present embodiment, only the holes 93 are shown covered by material 94, other portions of crimp sleeve 90 may be also covered to improved the electrical characteristics of electrode 59. In the present embodiment it is contemplated MCRD 92 would feature a drug to elute asteroid, such as the sodium phosphate of declamethosone. Of course, other compounds may be introduced into MCRD to be eluted therefrom.

While the embodiments of the present invention have been described in particular application to cardiac stimulation, the present invention may also be practiced in other electrode technologies where the aforementioned characteristics are desirable, including neurological and muscle stimulation applications, as well as other forms of electrically stimulating other body tissues or organs.

For example, the present invention is believed to be particularly suitable for the placement of a medical electrical lead onto the stomach for purposes of pacing the stomach. Further details regarding the use of electrical stimulation to pace a human stomach may be seen in the European Patent Application 93108399.2 "Retrograde Pacing of Stomach to Treat Obesity" of Valero Cigaina.

Furthermore, although the invention has been described in detail with particular reference to a preferred embodiment, it will be understood variations and modifications can be effected within the scope of the following claims. Such modifications may include substituting elements or components which perform substantially the same function in substantially the same way to achieve substantially the same result for those described herein.

What is claimed is:

1. A system for implanting a lead into body tissue comprising:

a first trocar having a lumen; and a lead positioned within the lumen, the lead having a needle, the needle having a first section and a second section, the first section being straight and the second section being curved;

a strand of suture connected to the needle;

a conductor coupled to the strand; and an insulative cover over part of the conductor.

2. The system according to claim 1, further comprising a crimp collar coupled to the strand and the conductor.

3. The system according to claim 2, wherein the suture is treated with an elutable drug.

4. The system according to claim 3, wherein the drug is a glucocorticosteroid.

5. The system according to claim 3 wherein the drug is an antibiotic.

6. The system according to claim 1 further comprising a test wire electrically coupled to the needle.

7. The system according to claim 6 wherein the test wire comprises a test conductor having a first end and a second end, the first end coupled to the needle, a test insulative cover insulating the test conductor between the first end and the second end.

8. The system according to claim 1 wherein the suture is coupled to the first section of the needle.

9. The system according to claim 1 wherein the second section of the needle has a radius of curvature of 13 mm over 30 degrees.

10. The system according to claim 1 wherein the first section has a length of 25 mm.

11. A system for stimulation of body tissue comprising:

a first trocar having a lumen; and a lead positioned within the lumen, the lead having a needle, the needle having a first section and a second section, the flint section being straight and the second section being curved;

a strand of suture connected to the needle;

an electrode coupled to the strand of suture;

a conductor coupled to the electrode suture;

an insulative cover covering at least a portion of the conductor;

terminal connector means coupled to the conductor; and a pulse generator coupled to the terminal connector means, the pulse generator emitting electrical stimulation signals.

12. The system of claim 11 further comprising the strand of suture having a coiled section.

13. The system of claim 11 further comprising a test wire electrically coupled to the needle.

14. The system according to claim 11 wherein the second section of the needle has a radius of curvature of 13 mm over 30 degrees.

15. The system according to claim 11 wherein the first section of the needle has a length of 25 mm.

* * * * *